(12) United States Patent
Sundar (10) Patent No.: US 6,979,348 B2
(45) Date of Patent: Dec. 27, 2005

(54) REFLOWED DRUG-POLYMER COATED STENT AND METHOD THEREOF

(75) Inventor: Rangarajan Sundar, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/454,652

(22) Filed: Jun. 4, 2003

(65) Prior Publication Data

US 2004/0249437 A1    Dec. 9, 2004

(51) Int. Cl.[7] .............................. A61F 2/06; B05D 1/34
(52) U.S. Cl. .................... 623/1.15; 623/901; 427/2.24; 427/348
(58) Field of Search .............................. 623/1.15, 1.46, 623/1.42, 901; 427/2.24, 2.25, 331, 348

(56) References Cited

U.S. PATENT DOCUMENTS

| | | |
|---|---|---|
| 4,771,929 A * | 9/1988 | Bahr et al. .................. 228/102 |
| 5,674,242 A | 10/1997 | Phan |
| 5,693,085 A | 12/1997 | Buirge et al. |
| 5,908,410 A | 6/1999 | Weber |
| 5,980,972 A | 11/1999 | Ding |
| 6,153,252 A | 11/2000 | Hossainy et al. |
| 6,214,115 B1 | 4/2001 | Taylor et al. |
| 6,361,759 B1 | 3/2002 | Frayne |
| 6,364,893 B1 | 4/2002 | Sahatjian et al. |
| 2004/0039437 A1 * | 2/2004 | Sparer et al. .............. 623/1.15 |

FOREIGN PATENT DOCUMENTS

WO    WO 00/62830    10/2000

* cited by examiner

Primary Examiner—David J. Isabella

(57) ABSTRACT

The present invention provides a method of forming a drug-polymer coated stent. A polymeric coating is applied onto at least a portion of a stent framework and dried. A jet of heated gas is directed towards excess coating portions of the dried polymeric coating. The excess coating portions, which extend into apertures of the stent framework, are removed from the apertures of the stent framework by reflowing the polymeric coating with the directed jet of heated gas. A drug-polymer coated stent with a reflowed drug-polymer coating and a system for treating a vascular condition are also disclosed.

12 Claims, 4 Drawing Sheets

REFLOWED DRUG-POLYMER COATED STENT AND METHOD THEREOF

FIELD OF THE INVENTION

This invention relates generally to biomedical stents. More specifically, the invention relates to a drug-polymer coated endovascular stent with a reflowed polymeric coating, and methods of coating thereof.

BACKGROUND OF THE INVENTION

Protective materials and bioactive drugs are used on medical devices for treating vascular conditions such as stents. With generally open cylindrical scaffolding, stents typically have apertured or lattice-like walls of a metallic or polymeric base, and can be either balloon expandable or self-expanding. A stent is typically deployed by mounting the stent on a balloon portion of a balloon catheter, positioning the stent in a body lumen, and expanding the stent by inflating the balloon. The balloon is then deflated and removed, leaving the stent in place. Stents help reduce the probability and degree of vessel blockage from restenosis.

Various approaches for providing localized drug delivery using coated stents have been under investigation and marketed for some time. A variety of stent coatings and compositions have been proposed to provide localized therapeutic pharmacological agents and treatment of a vessel at the site being supported by the stent. Stent coatings with various families of drug polymer chemistries have been used to increase the effectiveness of stenting procedures and to control drug-elution properties. For example, polymeric coatings can be made from polyurethane, polyester, polylactic acid, polyamino acid, polyorthoester, or polyphosphate ester. Examples of drug or bioactive agents include antirestonotic and anti-inflammatory compounds.

Medical research indicates a greater effectiveness of vascular stents when the stents are coated with pharmaceutical drugs that help prevent or treat medical conditions such as restenosis and thrombosis. These drugs may be released from a coating while in the body, delivering their patent effects at the site where they are most needed. The localized levels of the medications can be elevated, and therefore potentially more effective than orally or intravenously delivered drugs. Furthermore, drugs released from tailored stent coatings can have controlled, timed-release qualities, eluting their bioactive agents over hours, weeks or even months. Stent coatings typically have a drug or active agent, which has been dissolved or dispersed throughout the polymeric material and physically constrained within the polymer. The sustained release of drugs generally relies upon either controlled degradation of the polymer or diffusion through the polymer to control the elution of the compounds.

Stents can be coated with a polymer or combination of a polymer and a pharmaceutical agent or drug by application techniques such as dipping, spraying, painting, and brushing. Typical methods of coating, such as spraying, dipping and brushing techniques, can be susceptible to a degree of pooling, bridging, or webbing on stent structures and struts, problems recognized by those skilled in the art of manufacturing stents.

Several solutions have been suggested. One solution in a manual dipping process blows excessive material off an open stent framework, as disclosed in "Coating" by Taylor et al., U.S. Pat. No. 6,214,115 issued Apr. 10, 2001. The process addresses the problems of inconsistent drying and blockage of openings. Hossainy and others disclose another dipping process that addresses the issues of blockage and bridging between stent struts in "Process for Coating Stents", U.S. Pat. No. 6,153,252 issued Nov. 28, 2000. Flow or movement of the coating fluid through the openings in the perforated medical device is used to avoid the formation of blockages or bridges. The flow system may use a perforated manifold inserted in the stent to circulate the coating fluid, or may place the stent on a mandrel or in a small tube that is moved relative to the stent during the coating process.

Another coating method that uses airflow is disclosed in "Coating Medical Devices Using Air Suspension", Schwarz et al., International Patent Application WO 00/62830 published Oct. 26, 2000. The proposed method suspends a medical device in air and introduces a coating material into an air stream such that the material is dispersed therein to coat at least a portion of the device.

In addition to controlling any excessive coating material, an effective coating method needs to result in a lubricious or smooth outer surface of the coated stent, thereby reducing the probability of abrasions to body tissue as a stent is deployed. One coating method that optionally applies a solvent by dipping or spraying on an already coated stent to smooth the outer surface of the coating is described by Ding in "Method of Applying Drug-Release Coatings", U.S. Pat. No. 5,980,972 issued Nov. 9, 1999. The method uses two solutions: one with a polymer dissolved in a first solvent and another with a drug dissolved or suspended in a second solvent. When a third solvent is used to smooth the stent coating, the solvent needs to be compatible with the polymer matrix.

In another example, a collagen liner material forms a lubricious surface over the stent to protect the vascular wall and form a non-thrombogenic cushion for the stent in the vascular lumen, as disclosed in "Stent with Collagen", Buirge et al., U.S. Pat. No. 5,693,085 issued Dec. 2, 1997.

Another smooth stent surface is described in "Stent Lining", Sahatjian et al., U.S. Pat. No. 6,364,893, issued Apr. 2, 2002. A stent is lined with a hydrogel to reduce shear forces and flow disturbances in the blood, to protect damaged cells adjacent to the stent, to reduce platelet deposition at the stent site, and to deliver a drug to reduce or prevent restenosis of stent lumens. The expandable stent is mounted on a catheter balloon, which is coated with a hydrogel. The stent is delivered in a contracted condition to a targeted site in a body where the expanding balloon lodges the stent in the body with the hydrogel coated on the inner surfaces of the stent as a lining.

Drug polymer coatings on medical devices need to adhere well to the substrate or surface of the medical device and be mechanically pliant, because the devices often undergo significant flexion or expansion during the delivery and deployment. Excess coating material that can occur between struts of the stent needs to be removed or controlled to prevent cracking or flaking during or after the deployment of the stent. A stent deployed by self-expansion or balloon expansion is accompanied by a high level of bending at portions of the stent framework, which can cause cracking, flaking, peeling, or delaminating of many candidate drug polymers when the stent diameter is increased by threefold or more during expansion. In addition, any step within the process for coating a pre-deployed stent should not cause a drug-polymer to fall off, crystallize or melt.

Accordingly, a desirable, efficient and improved coating method would provide a well-adhered coating with a smooth outer surface of a medical device. In addition, the method would minimize or eliminate the pooling, bridging, or webbing of excess coating material between structures such as stent struts. In addition, the stent associated with this method has a smoother coating topography with one or more well adhered drug-polymer coatings that maintain mechanical integrity during stent deployment and provide a desired elution rate for one or more drugs, overcoming the deficiencies and limitations described above.

SUMMARY OF THE INVENTION

One aspect of the invention provides a method of forming a drug-polymer coated stent. A polymeric coating is applied onto at least a portion of a stent framework and dried. A jet of heated gas is directed towards excess coating portions of the dried polymeric coating that extend into apertures of the stent framework. The polymeric coating is reflowed with the directed jet of heated gas, removing the excess coating portions from the apertures of the stent framework.

Another aspect of the invention provides a drug-polymer coated stent, including a stent framework and a drug-polymer coating disposed on the stent framework. The drug-polymer coating includes a reflowed portion proximate to apertures in the stent framework.

Another aspect of the invention provides a system for treating a vascular condition, including a catheter and a drug-polymer coated stent coupled to the catheter. The drug-polymer coated stent includes a stent framework having a reflowed portion proximate to apertures in the stent framework.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein.

DETAILED DESCRIPTION OF THE PRESENTLY PREFERRED EMBODIMENTS

Figure 1:
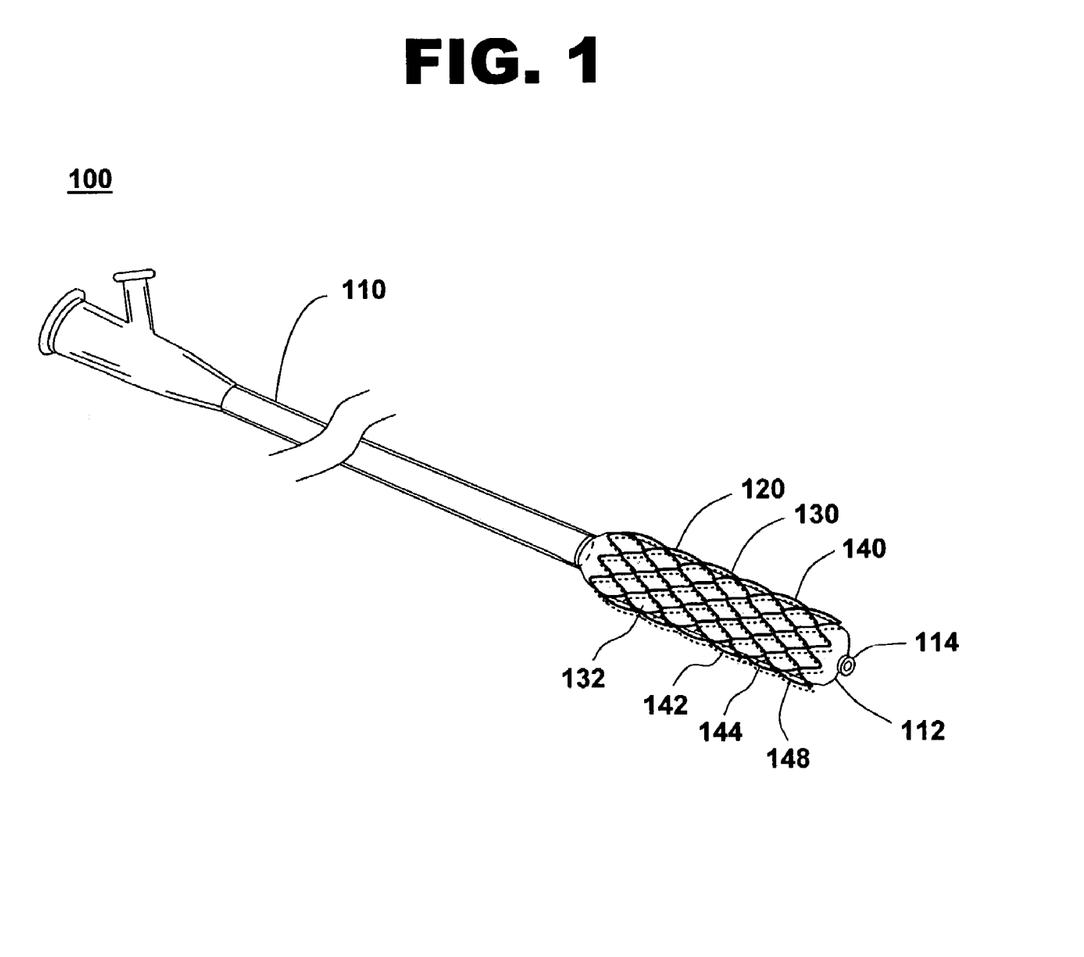
FIG. 1 is an illustration of a system for treating a vascular condition including a drug-polymer coated stent coupled to a catheter, in accordance with one embodiment of the current invention.

FIG. 1 illustrates a system for treating a vascular condition, comprising a drug-polymer coated stent coupled to a catheter, in accordance with one embodiment of the present invention at 100. Vascular condition treatment system 100 includes a drug-polymer coated stent 120 coupled to a delivery catheter 110. Coated stent 120 includes a stent framework 130 and a reflowed drug-polymer coating 140 disposed on at least a portion of stent framework 130. Generally tubular in shape with open ends, the latticework of stent framework 130 has a plurality of open apertures 132 between the struts, shaped to allow expansion of stent framework 130 from an initially contracted form when deployed.

Drug-polymer coating 140 includes a polymeric coating 142 positioned adjacent to stent framework 130 and at least one therapeutic agent 144 encased by or interdispersed within drug-polymer coating 140. In some cases, drug-polymer coating 140 includes a cap coating 148 disposed on reflowed drug-polymer coating 140. Drug-polymer coating 140 can provide time-released delivery of one or more therapeutic agents to surrounding tissue after coated stent 120 has been deployed within a vessel of the body.

Insertion of coated stent 120 into a vessel in the body helps treat, for example, heart disease, various cardiovascular ailments, and other vascular conditions. Catheter-deployed coated stent 120 typically is used to treat one or more blockages, occlusions, stenoses, or diseased regions in the coronary artery, femoral artery, peripheral arteries, and other arteries in the body. Treatment of vascular conditions involves the prevention or correction of various ailments and deficiencies associated with the cardiovascular system, the cerebrovascular system, urinogenital systems, biliary conduits, abdominal passageways and other biological vessels within the body.

An exemplary drug-polymer coating 140 includes or encapsulates one or more therapeutic agents. Drug-polymer coating 140 may comprise one or more therapeutic agents 144 dispersed within or encased by drug-polymer coating 140 on coated stent 120, which are eluted from coated stent 120 with controlled time delivery after deployment of coated stent 120 in the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constricting of the diameter of the bodily lumen where the stent is placed. Drug-polymer coating 140 may comprise, for example, an antirestenotic drug such as rapamycin, a rapamycin analogue, or a rapamycin derivative to prevent or reduce the recurrence or narrowing and blockage of the bodily vessel. Drug-polymer coating 140 may comprise an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof.

The elution rates of the therapeutic agents and total drug eluted into the body and the tissue bed surrounding the stent framework are based on the thickness of drug-polymer coating 140; the constituency of drug-polymer coating 140; the nature, distribution and concentration of the therapeutic agents; the thickness and composition of any cap coat, and other factors. Drug-polymer coating 140 may include and elute multiple therapeutic agents to achieve the desired therapeutic effect. Drug-polymer coating 140 can be tailored to control the elution of one or more therapeutic agents that are transported through the coating primarily by diffusion processes. In some cases, a portion of the polymeric coating is absorbed into the body, releasing therapeutic agents embedded within or encased by the coating. In other cases, drug-polymer coating 140 erodes from coated stent 120 to release the therapeutic agents, the residual polymer being expelled by the body. Cap coating 148 can be selected to provide a diffusion barrier to the therapeutic agents and aid in the control of drug elution.

Incorporation of a drug or other therapeutic agents into drug-polymer coating 140 allows, for example, the rapid delivery of a pharmacologically active drug or bioactive agent within twenty-four hours following the deployment of a stent, with a slower, steady delivery of a second bioactive agent over the next three to six months. For example, the therapeutic agent may comprise an antirestenotic drug such as rapamycin, a rapamycin analogue, or a rapamycin derivative. A second therapeutic agent may comprise, for example, an anti-inflammatant such as dexamethasone. The therapeutic agent constituency in the drug-polymer coating may be, for example, between 0.1 percent and 50 percent of the drug-polymer coating by weight.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a contrast fluid that fills a tube inside catheter 110 and balloon 112. Coated stent 120 is expanded until a desired diameter is reached, and then the contrast fluid is depressurized or pumped out, separating balloon 112 from coated stent 120 and leaving coated stent 120 deployed in the vessel. Alternatively, catheter 110 may include a sheath that retracts, allowing the expansion of a self-expanding version of coated stent 120.

Figure 2:
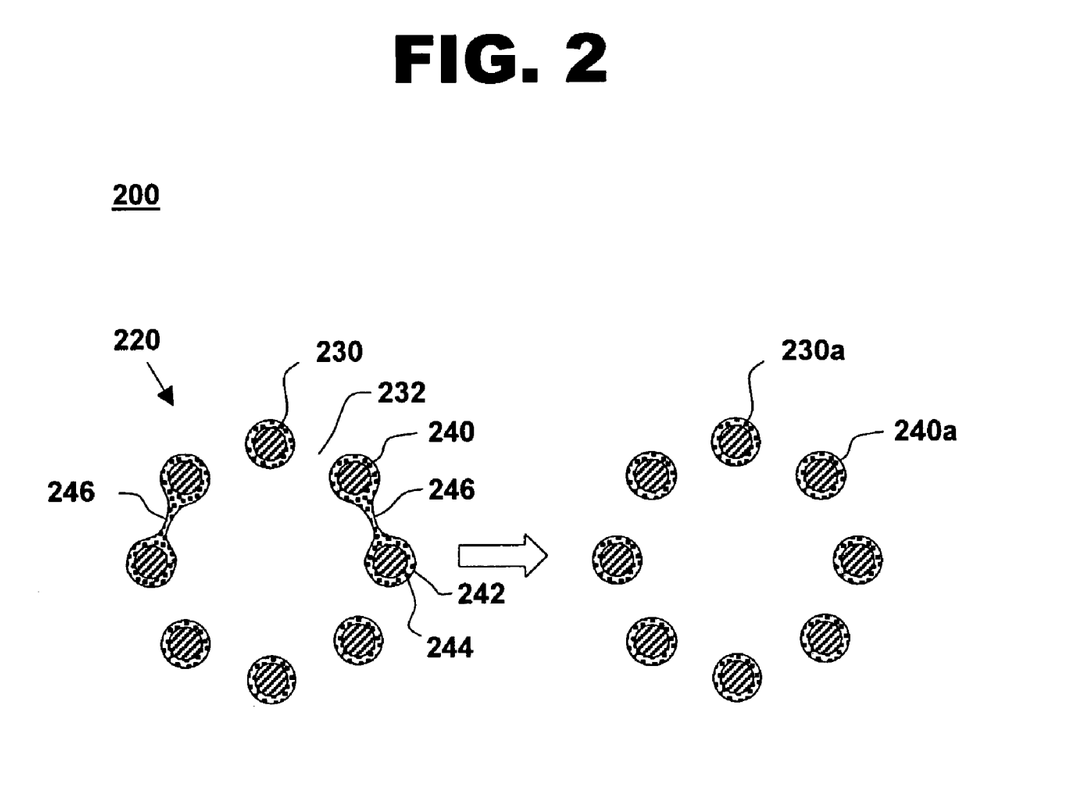
FIG. 2 is a cross-sectional view of a drug-polymer coated stent, in accordance with one embodiment of the current invention.

FIG. 2 shows a cross-sectional view of a drug-polymer coated stent, in accordance with one embodiment of the present invention at 200. A drug-polymer coated stent 220 includes a stent framework 230 with a drug-polymer coating 240 disposed on stent framework 230. Drug-polymer coating 240 includes a polymeric coating 242 positioned adjacent to stent framework 230 and a therapeutic agent 244 encased by or interdispersed within polymeric coating 242.

Drug-polymer coating 240 typically encases stent framework 230, forming a relatively thin coating around the struts and latticework of stent framework 230. During processing, one or more excess coating portions 246 may occur in apertures 232 of stent framework 230 between the struts and open areas of the latticework. During coating operations such as dipping, spraying, brushing or painting, polymeric solution may pool, web, or bridge in apertures 232, resulting in one or more excess coating portions 246, particularly near places where stent framework 230 is held. Excess coating portions 246 can be removed from apertures 232 of stent framework 230 by heating and reflowing polymeric coating 242, resulting in a reflowed drug-polymer coating 240a around stent framework 230a proximate to apertures 232 in stent framework 230 with excess portions 246 removed from apertures 232. Reflowing drug-polymer coating 240 or polymeric coatings 242 may also result in improved surface smoothness of the coating and enhanced adhesion to the metallic or polymeric base of stent framework 230 or to any underlying coatings.

Stent framework 230 comprises a metallic base or a polymeric base, such as stainless steel, nitinol, tantalum, MP35N alloy, platinum, titanium, a chromium-based alloy, a cobalt-based alloy, a suitable biocompatible alloy, a suitable biocompatible material, a biocompatible polymer, or a combination thereof. The polymeric base material may comprise any suitable polymer for biomedical stent applications, as is known in the art.

Drug-polymer coating 240 includes a polymeric coating 242 with a polymer such as poly(vinyl alcohol) (PVA), poly(ethylene-vinyl acetate) (PEVA), polyurethane (PU), polycaprolactone (PCL), polyglycolide (PGA), poly(lactide-co-glycolide) (PLGA), poly(ethylene oxide) (PEO), poly (vinyl pyrrolidone) (PVP), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, or a combination thereof. The polymer may be applied using a technique such as dipping or spraying with limited drying or limited crosslinking to achieve the desired level of tackiness.

Drug-polymer coating 240 comprises at least one therapeutic agent 244. Therapeutic agent 244 may be mixed with polymeric coating 242 prior to the application of drug-polymer coating 240, or added to polymeric coating 242 after the application of polymeric coating 242 onto stent framework 230. Therapeutic agent 244 may be in any suitable form such as a liquid, a gel, a powder, a particle, a granulated drug, a micronized drug, a pelletized drug, a microencapsulated drug, a nanoencapsulated drug, or a combination thereof.

Although illustrated with one layer of drug-polymer coating 240, multiple coatings of the polymer or drug-polymer may be disposed on stent framework 230 to provide a thicker composite coating and a larger quantity of therapeutic agents. Multiple therapeutic agents may be arranged within drug-polymer coating 240 to provide a control time-delivery of each therapeutic agent. For example, tailoring the thickness and constituency of each drug-polymer coating 240, the distribution and concentration of the therapeutic agents, and inclusion of an optional cap coating helps control the elution rate of one or more therapeutic agents dispersed within or encased by drug-polymer coating 240. Drug elution refers to the transfer of a therapeutic agent from drug-polymer coating 240 to the surrounding area in a body. The amount of drug eluted is determined as the total amount of therapeutic agent excreted out of drug-polymer coating 240, typically measured in units of weight such as micrograms, or in weight per peripheral area of the stent. The concentration of the therapeutic agent included with drug-polymer coating 240 is between, for example, 0.1 percent and 50 percent by weight.

Figure 3:
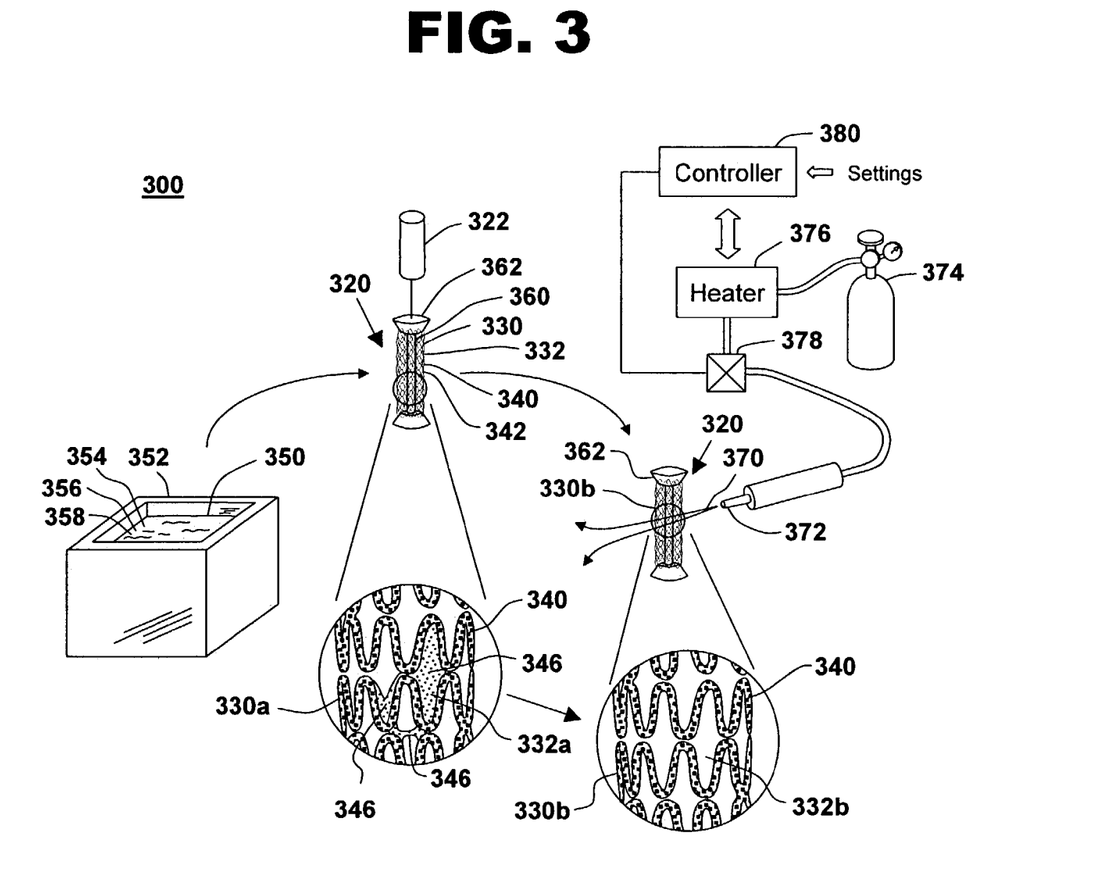
FIG. 3 is an illustration of a system for forming a drug-polymer coated stent, in accordance with one embodiment of the current invention.

FIG. 3 shows an illustration of a system for forming a drug-polymer coated stent, in accordance with one embodiment of the current invention at 300. Drug-polymer coating system 300 includes a polymeric solution 350 in a dipping tank 352 and a transport mechanism 322 such as a clamp or a tether for holding and transporting stents in and out of tank 352 either manually or automatically. Multiple stent frameworks 330 are readily accommodated for dipping and drying in a batch or continuous batch process. A mandrel 360 with cones 362 at each end of stent framework 330 may be used, for example, to hold stent framework 330 during dipping and reflowing.

In one example, polymeric solution 350 includes at least one polymer 354, a therapeutic agent 356, and a solvent 358. Stent framework 330 is dipped into polymeric solution 350 and dried, for example, by positioning the dipped stent framework 330 in air and evaporating much or all of solvent 358 to form a drug-polymer coating 340 on stent framework 330. The components of polymeric solution 350 and the dipping treatments are selected to provide a drug-polymer coating 340 on stent framework 330 with the desired thickness and quantity of therapeutic agents. In one example, polymeric solution 350 includes a polymer 354 such as poly(vinyl alcohol), poly(ethylene-vinyl acetate), polyurethane, polycaprolactone, polyglycolide, poly(lactide-co-glycolide), poly(ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, or a combination thereof, along with a suitable solvent 358 that is compatible with polymer 354 and the therapeutic agents 356. In another example, drug-polymer coating 340 is applied onto stent framework 330 by spraying or brushing. Stent framework 330 is generally dipped into polymeric solution 350 for a prescribed period of time, and removed for drying in air or in an oven. Additional dipping or spraying steps may be used to achieve a thicker drug-polymer coating 340. Drug-polymer coating 340 can be baked in an oven at an elevated temperature to further drive off buried pockets of solvent and to provide a desired level of crosslinking of the polymers.

After applying polymeric coating 342 onto at least a portion of stent framework 330 and drying applied polymeric coating 342, coated stent 320 may have excess coating portions 346 extending from the struts and latticework into apertures 332 of stent framework 330. In the detailed view, drug-polymer coating 340 has excess coating portions 346 with one or more webbed regions, pooled regions, bridged regions, or combinations thereof extending into apertures 332a of stent framework 330a. Coated stent 320 with excess coating portions 346 may be positioned in front of a jet of heated gas 370 emitted from a gas nozzle 372. Apertures 332 of stent framework 330 with excess coating portions 346 may be positioned adjacent to jet of heated gas 370. Dried polymeric coating 342 may be heated above a reflow temperature of dried polymeric coating 342. Dried polymeric coating 342 is reflowed with the directed jet of heated gas 370 to remove excess coating portions 346 from apertures 332 of stent framework 330.

The heated gas 370 ejected from gas nozzle 372 may be supplied, for example, from a pressurized gas tank 374 and heated in a heater 376. The heated gas 370 may be adjusted and controlled with a gas valve 378 by a microprocessor-controlled controller 380. Controller 380 may be automatic or semi-automatic, receiving, commands and settings from a user or a control computer to appropriately position coated stent 320, pressurizing and heating gas 370, and adjusting the ejection temperature and the ejection velocity of the ejected gas 370. In a fully automatic system, positioning and inspection capability can be added for real-time control and inspection to determine excess coating portions 346 and remove them. In one example of a manual system, the temperature of the heated gas is controlled and the gas velocity is manually controlled. A filter may be included to remove particles from gas 370.

After the reflow of polymeric coating 342 has been completed and the coated stent 320 has cooled, excess coating portions 346 have been removed and apertures 332b of stent framework 330b are clear of any excess coating portions 346, leaving drug-polymer coating 340 on the struts and latticework of stent framework 330b, as shown in the detailed view of stent framework 330b.

Multiple dipping, drying and reflow steps can be used to apply additional drug-polymer coatings 340 or other polymeric coatings 342 onto stent framework 330. The reflow steps can be used to clear bridging, pooling and webbing of excess polymer and drug polymer after one or more applications of a primer coating, a drug-polymer coating, a cap coating, or a combination thereof.

Figure 4:
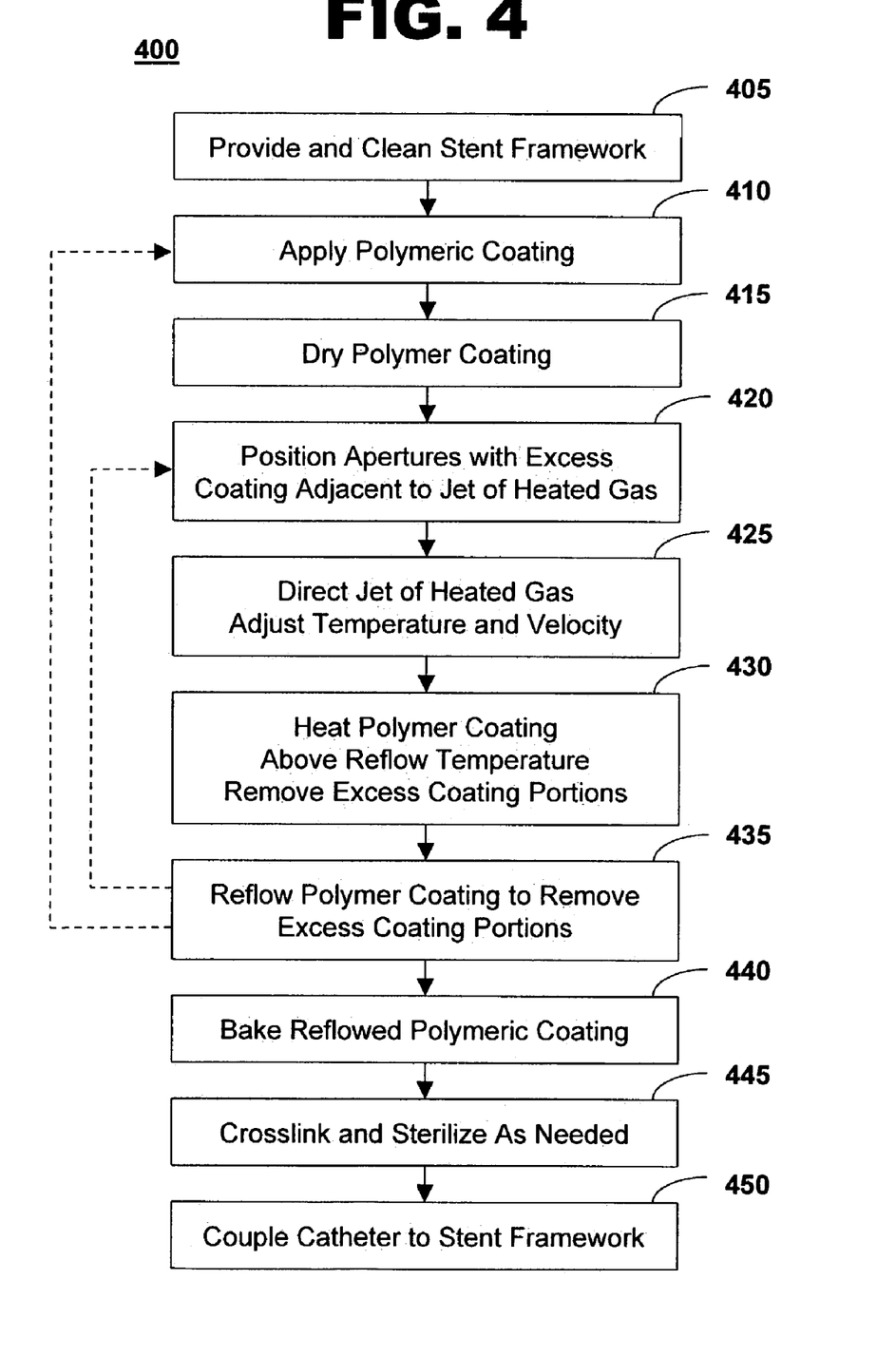
FIG. 4 is a flow diagram of a method of forming a drug-polymer coated stent, in accordance with one embodiment of the current invention.

FIG. 4 shows a flow diagram of a forming a drug-polymer coated stent, in accordance with one embodiment of the present invention at 400. Drug-polymer application method 400 includes various steps to form and reflow a drug-polymer coating on a stent framework with an optional primer coating or an optional cap coating.

A stent framework is provided and cleaned, as seen at block 405. The stent framework may be cleaned, for example, by inserting the stent framework into various solvents, degreasers and cleansers to remove any debris, residues, or unwanted materials from the surface of the stent framework. The stent framework is dried, and generally inspected at this point in the process. Generally, a primer coating is not required, though a primer coating may be applied to the stent framework prior to application of the polymer or drug-polymer coating. The primer coating is dried to eliminate or remove any volatile components and then cured or crosslinked as needed. Excess liquid may be blown off prior to drying the primer coating, which may be done at room temperature or at elevated temperatures under dry nitrogen or other suitable environments including a vacuum environment.

A polymeric coating is applied onto at least a portion of the stent framework, as seen at block 410. The polymeric coating may comprise, for example, a primer coating, a drug-polymer coating, a cap coating, or a combination thereof. The polymeric coating is applied using any suitable coating technique such as dipping, spraying, painting, or brushing. Exemplary applied polymeric coatings comprise polymers such as poly(vinyl alcohol), poly(ethylene-vinyl acetate), polyurethane, polycaprolactone, polyglycolide, poly(lactide-co-glycolide), poly(ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, and combinations thereof. In one embodiment of the present invention, one or more therapeutic agents may be added to and dispersed within the polymeric coating before its application onto the stent framework.

The dipped, sprayed or brushed stent framework is then dried, as seen at block 415. The coated stent framework may be dried, for example, by positioning the coated stent framework in air and evaporating any solvent from the applied polymeric coating. The polymeric coating is generally dried after application by evaporating off the solvent at room temperature and under ambient conditions. A nitrogen environment or other controlled environment may also be used for drying. Alternatively, the polymeric coating can be dried by evaporating the majority of any solvent at room temperature, and then further drying the coating in a vacuum environment between, for example, a room temperature of about 25 degrees centigrade and 50 degrees centigrade or higher. Drying in a vacuum environment helps to extract any pockets of solvent buried within the polymeric coating and to provide the desired level of crosslinking in the polymer. After application and drying of the polymeric coating, excess coating portions may extend into apertures of the stent framework by webbing, pooling or bridging of the polymeric coating between struts and latticework of the stent framework.

The apertures of the stent framework that have excess coating portions may be positioned adjacent to a jet of heated gas, as seen at block 420. The coated stent framework may be positioned manually or automatically such that a portion of the stent framework with the excess coating portions is placed in front of jet of heated gas. The heated gas may be emitted from, for example, one or more gas nozzles, one or more holes in a manifold positioned near the coated stent framework, or from a series of holes in a mandrel that is holding the coated stent framework with cups or cones at each end.

One or more jets of heated gas are directed towards excess coating portions of the dried polymeric coating, as seen at block 425. The excess coating portions extend into apertures of the stent framework. The heated gas is directed onto the excess coating portions, softening and sometimes melting the polymeric material. For example, the directed jet of heated gas may be pressurized and ejected from a gas nozzle or from holes in a tube or manifold. In some cases, the jets of heated gas are directed or scanned along the entire coated stent framework; in other cases, the heated gas is emitted from one or more gas nozzles and directed at only the excess coating portions. The directed jet of heated gas may comprise, for example, a gas such as nitrogen, argon, or air. A filter may be used to remove large particles from the jets of heated gas.

The temperature and velocity of the heated gas may be adjusted, for example, to effectively remove excess coating portions from the apertures and to reflow the polymeric coating onto the stent framework. The temperature of the directed jet of heated gas may have an ejection temperature, for example, between 25 degrees centigrade and 500 degrees centigrade, although a typical ejection temperature is between 100 degrees centigrade and 150 degrees centigrade. The type of polymer and drug used in the formulation may impose limits on the temperature of the heated gas. The velocity of the directed jet of heated gas may have an ejection velocity, for example, of greater than two meters per second.

The dried polymeric coating may be heated close to or above a reflow temperature of the dried polymeric coating, as seen at block 430. For example, a polymeric coating with a glass transition temperature of 150 degrees centigrade may be heated to a reflow temperature of 140 degrees where the polymeric coating is soft and can reflow. In another example, the excess coating portions are locally heated to a reflow temperature above the glass transition temperature, so that the excess polymeric coating liquefies and is blown away or reflows onto the coated stent framework where it cools and hardens. In another example, the coated stent framework is pre-heated prior to directing heated gas into the apertures and reflowing the excess coating portions.

The polymeric coating is reflowed to remove excess coating portions, as seen at block 435. The polymeric coating may be reflowed by heating the polymeric coating with directed jets of heated gas for a sufficient period of time so that excess coating portions from the apertures of the stent framework are removed. Excess coating portions may be caused, for example, by webbing, pooling or bridging between struts and open spaces in the latticework of the stent framework. Excess coating portions may occur near the ends of the stent framework where the stent framework is held with cones or cups to a mandrel, or at frayed regions where the holding apparatus has been removed. The reflowed polymeric coating may be blown off the stent framework, although the polymeric coating is usually heated to melt and fuse the excess coating portions proximate to the apertures in the stent framework. When heated, the polymeric coating generally reflows and reshapes around the struts and latticework of the stent framework. Reflowing the polymeric coatings and drug-polymer coatings, in addition to alleviating bridging, pooling and webbing, may also improve surface smoothness of the coatings and enhance adhesion to the stent framework or any underlying coatings. After the removal of the heated gas, the polymeric coating and the stent framework is cooled.

The coated stent framework with the reflowed polymeric coating may be re-positioned, as seen back at block 420, to remove excess coating portions from any remaining untreated apertures, until all excess coating portions have been removed from the apertures.

The polymeric coating may be reflowed and excess coating portions removed at the end of each application and drying step, such as after an application of a primer coating, after an application of each drug-polymer coating, and after an application of a cap coating. Additional coatings may be applied to the coated stent framework, as seen back at block 410. Subsequent coatings may be applied, for example, by repeated dipping into the same polymeric solution in a dipping tank. Other coatings may be applied, for example, by dipping the coated stent framework into a separate tank with another polymeric solution comprising a different polymer or a different therapeutic agent. The thickness, constituency and concentrations of the various layers can be applied and controlled to achieve the desired coating structure.

For example, a cap coating may be applied onto the polymer-coated stent framework. The cap coating is applied by using, for example, any suitable application technique such as dipping, spraying, brushing or painting. The cap coating provides a level of scratch and abrasion resistance during the handling of the coated stent, and can serve as a diffusion barrier that provides additional control over the elution of therapeutic agents from the drug-polymer coating after deployment of the stent within the body. The cap coating may be formed from polymers such as polycaprolactone, polyglycolide, poly(lactide-co-glycolide), a silicone-urethane copolymer, a polyurethane, or poly(ethylene-vinyl acetate). Multiple cap coats may be applied to achieve a thicker cap coating.

The reflow process allows for a higher concentration of solids in the polymeric solution during dipping or spraying, requiring less solvent and providing for a thicker coating on the stent framework without bridging, pooling or webbing.

The reflowed polymeric coating may be baked after removing the excess coating portions from the apertures of the stent framework, as seen at block 440. The reflowed polymeric coating may be baked in an oven under an inert environment such as nitrogen or vacuum, removing any remaining solvent and providing for further crosslinking of the polymeric coating. For example, the coated stent framework with the reflowed polymeric coating may be dried in a vacuum oven at 45 degrees centigrade for twenty minutes or more.

Other variations such as the application and reflowing of a drug-polymer coating prior to application of a cap coating are possible and within the spirit and scope of the present invention.

The coated stent may be crosslinked and sterilized as needed, as seen at block 445. Crosslinking may be done by providing additional drying cycles in air, or by heating the coated stent above a curing temperature in an oven with a controlled ambient such as vacuum, nitrogen, or air. Sterilization may employ, for example, gamma-ray irradiation, e-beam radiation, ethylene oxide gas, or hydrogen peroxide gas plasma sterilization techniques. The coated stent may be packaged, shipped, and stored in a suitable package until it is used.

A delivery catheter may be coupled to the coated stent, as seen at block 450. The delivery catheter may include an inflatable balloon that is positioned between the coated stent and the catheter and used for deploying the coated stent in the body. Alternatively, the delivery catheter may include a sheath that retracts to deploy a self-expanding version of the coated stent.

In one exemplary method, fully processed coated stents are reduced in diameter and placed into the distal end of the catheter to form an interference fit, which secures the stent onto the catheter. The catheter with the stent may be placed in a catheter package and sterilized prior to shipping and storing. Before clinical use, the stent is sterilized by any appropriate or medically conventional means.

When ready for deployment, the drug-polymer coated stent is inserted into a vessel of the body. The drug-polymer coated stent is inserted typically in a controlled environment such as a catheter lab or hospital. The delivery catheter, which helps position the drug-polymer coated stent in a vessel of the body, is typically inserted through a small incision of the leg and into the femoral artery, and directed through the vascular system to a desired place in the vessel. Guide wires threaded through an inner lumen of the delivery catheter assist in positioning and orienting the drug-polymer coated stent. The position of the drug-polymer coated stent may be monitored, for example, with a fluoroscopic imaging system or an x-ray viewing system in conjunction with radiopaque markers on the coated stent, radiopaque markers on the delivery catheter, or contrast fluid injected into an inner lumen of the delivery catheter and into an inflatable catheter balloon that is coupled to the drug-polymer coated stent. The stent is deployed, for example, by expanding the stent with a balloon or by extracting a sheath that allows a self-expandable stent to enlarge after positioning the stent at a desired location within the body.

Once the coated stent is deployed, the therapeutic agents in the drug-polymer coating are eluted. The elution rates of the therapeutic agents into the body and the tissue bed surrounding the stent framework are based on the polymers, thickness of the drug-polymer coating and any cap coating, and the distribution and concentration of the therapeutic agents contained therein, among other factors.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A method of forming a drug-polymer coated stent, comprising:
   applying a polymeric coating onto at least a portion of a stent framework;
   drying the applied polymeric coating on the stent framework;
   directing a jet of heated gas towards excess coating portions of the dried polymeric coating, the excess coating portions extending into apertures of the stent framework; and
   reflowing the polymeric coating with the directed jet of heated gas to remove the excess coating portions from the apertures of the stent framework.

2. The method of claim 1 wherein applying the polymeric coating onto the stent framework comprises one of dipping, spraying, or brushing the stent framework with a polymeric solution.

3. The method of claim 1 wherein the applied polymeric coating comprises at least one of a primer coating, a drug-polymer coating, or a cap coating.

4. The method of claim 1 wherein drying the applied polymeric coating on the stent framework comprises evaporating a solvent from the applied polymeric coating.

5. The method of claim 1 wherein the directed jet of heated gas comprises a gas selected from the group consisting of nitrogen, argon, and air.

6. The method of claim 1 wherein the directed jet of heated gas is pressurized and ejected from a gas nozzle.

7. The method of claim 1 wherein the directed jet of heated gas has an ejection temperature between 25 degrees centigrade and 500 degrees centigrade.

8. The method of claim 1 wherein the directed jet of heated gas has an ejection velocity greater than two meters per second.

9. The method of claim 1 further comprising:
   positioning the apertures of the stent framework with the excess coating portions adjacent to the jet of heated gas.

10. The method of claim 1 further comprising:
    heating the dried polymeric coating above a reflow temperature of the dried polymeric coating.

11. The method of claim 1 further comprising:
    adjusting an ejection velocity and an ejection temperature of the directed jet of heated gas.

12. The method of claim 1 further comprising:
    baking the reflowed polymeric coating after removing the excess coating portions from the apertures of the stent framework.

* * * * *